United States Patent [19]

Smith et al.

[11] Patent Number: 4,799,484

[45] Date of Patent: Jan. 24, 1989

[54] TAPERED I-BEAM SURGICAL NEEDLES

[75] Inventors: Daniel J. Smith, Manalapan Township, Monmouth County; Dennis L. Furman, East Windsor, both of N.J.

[73] Assignee: Ethicon, Inc., Somerville, N.J.

[21] Appl. No.: 36,723

[22] Filed: Apr. 10, 1987

[51] Int. Cl.$^4$ .............................................. A61B 17/04
[52] U.S. Cl. ........................................ 128/339; D24/26
[58] Field of Search ..................... 128/339; D24/26; 273/420, 419; 112/28, 154

[56] References Cited

U.S. PATENT DOCUMENTS

| | | | |
|---|---|---|---|
| 1,506,262 | 8/1924 | Slater | 128/339 |
| 2,841,150 | 7/1959 | Riall | 128/339 |
| 2,878,979 | 3/1959 | Lippard | 223/102 |
| 3,038,475 | 6/1962 | Orcutt | 128/339 |
| 3,160,157 | 12/1964 | Chisman | 128/339 |
| 3,197,997 | 8/1965 | Kurtz | 72/377 |
| 3,238,942 | 3/1966 | Lincoff | 128/339 |
| 3,386,438 | 6/1968 | Stevens | 128/334 R |
| 4,128,351 | 12/1978 | Kurtz et al. | 128/339 |

FOREIGN PATENT DOCUMENTS 3539891  11/1986  Fed. Rep. of Germany ...... 128/339

*Primary Examiner*—Richard C. Pinkham
*Assistant Examiner*—Gary Jackson

[57] ABSTRACT

Surgical needles are described which exhibit a tapered region intermediate the point and barrel sections, over which the needles undergo a gradual transition in shape from a generally rounded circumference to a rectangular I-beam shape. The I-beam shape affords favorable strength characteristics and the gradual transition in shape smoothes the changes in penetration force performance.

12 Claims, 4 Drawing Sheets

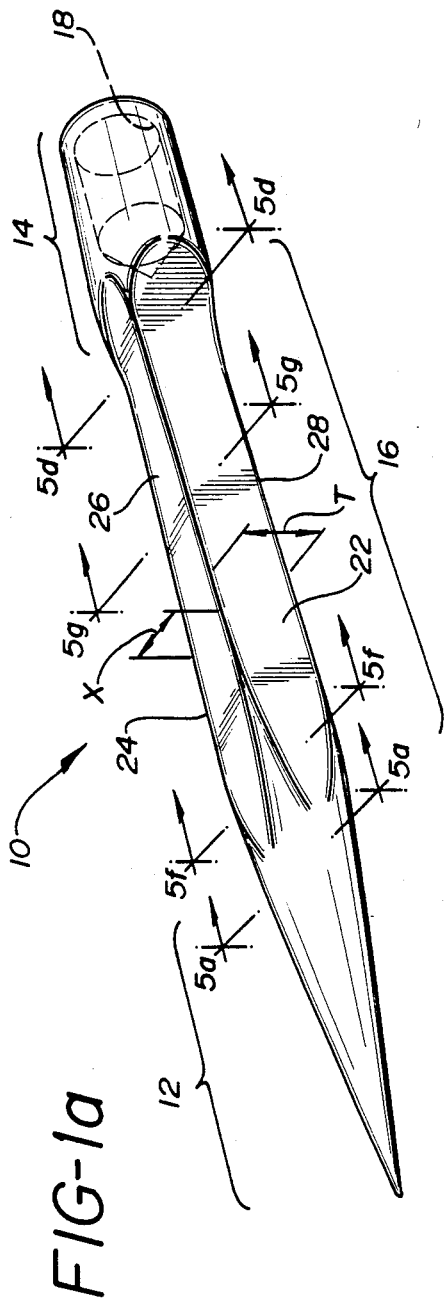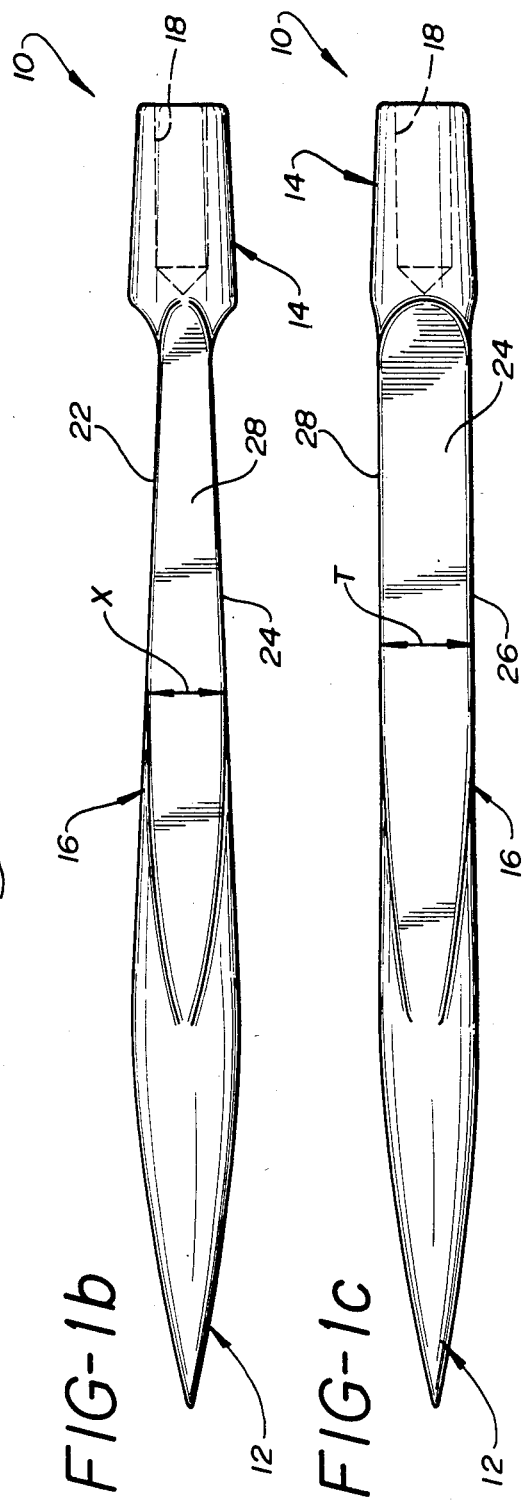

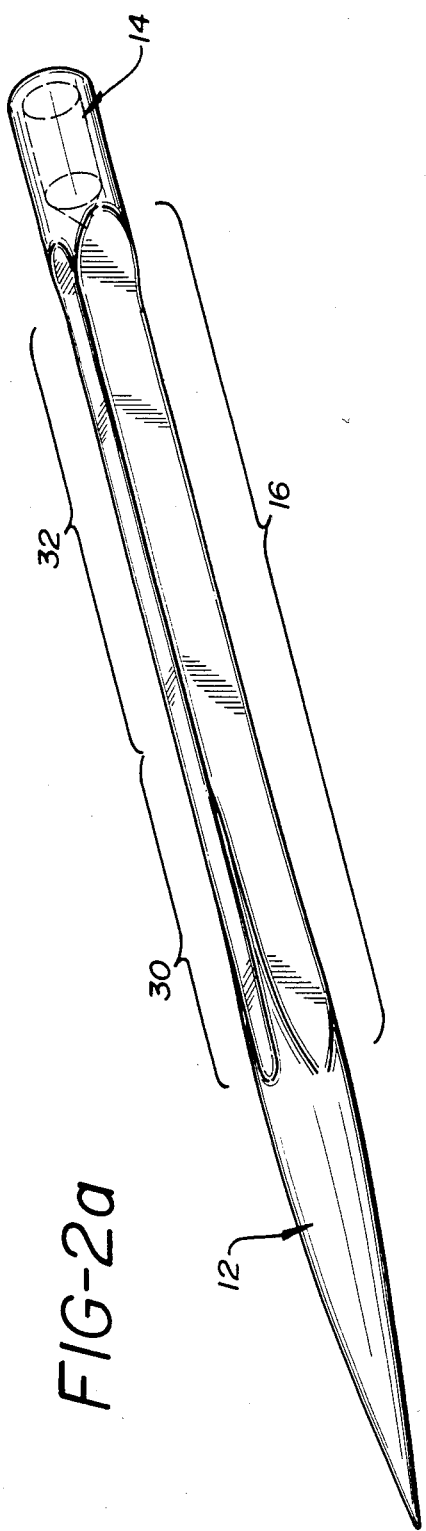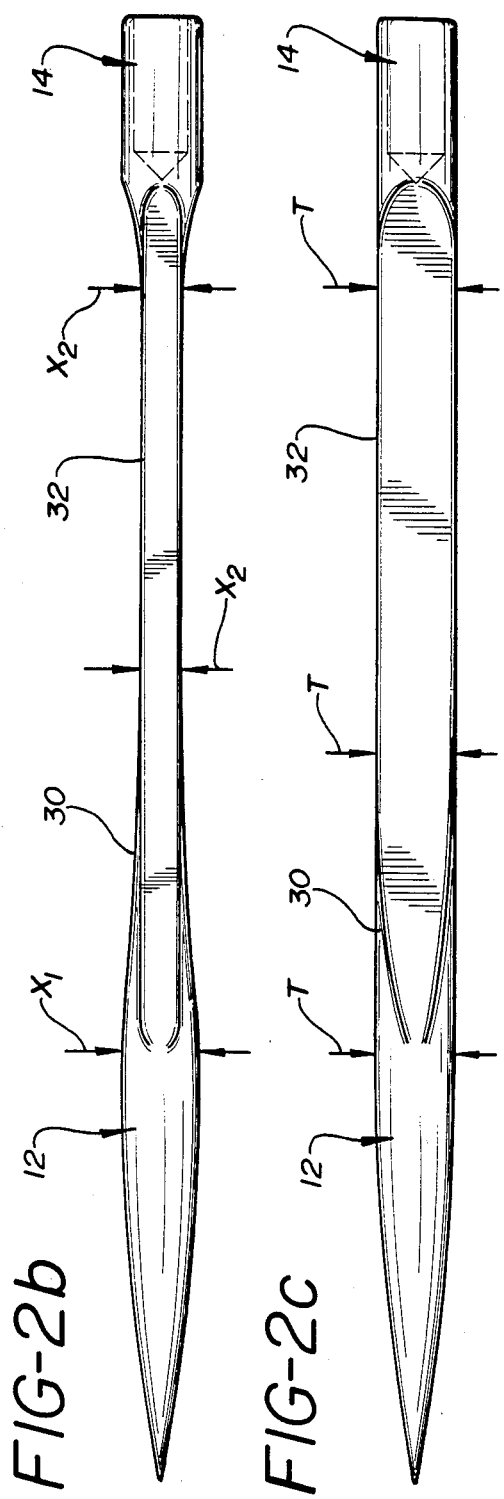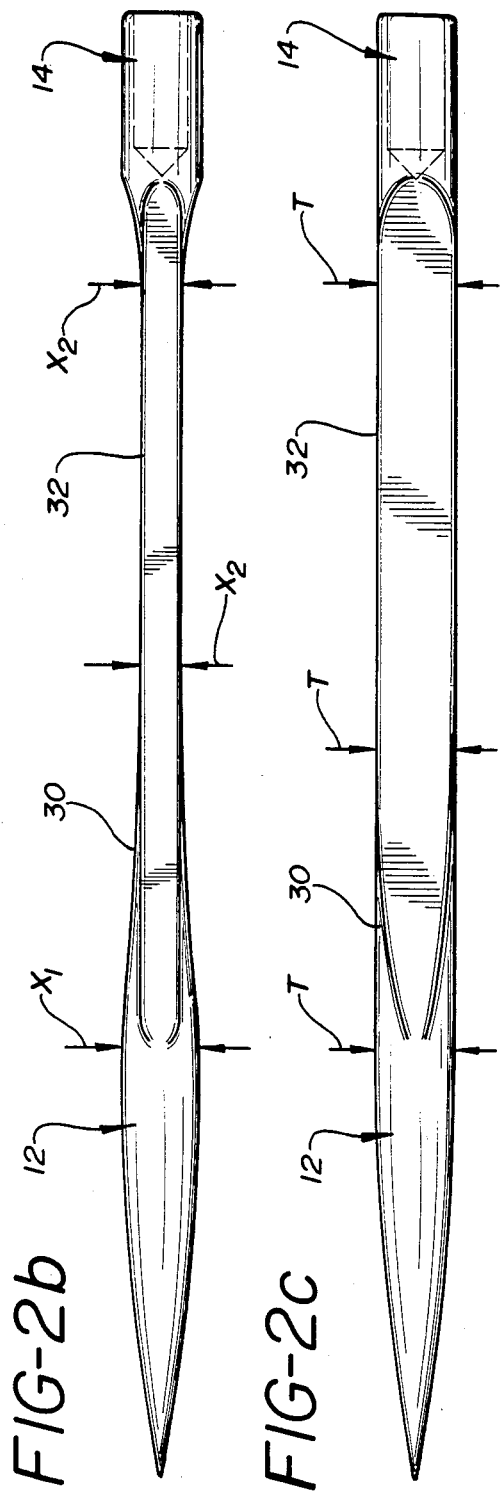

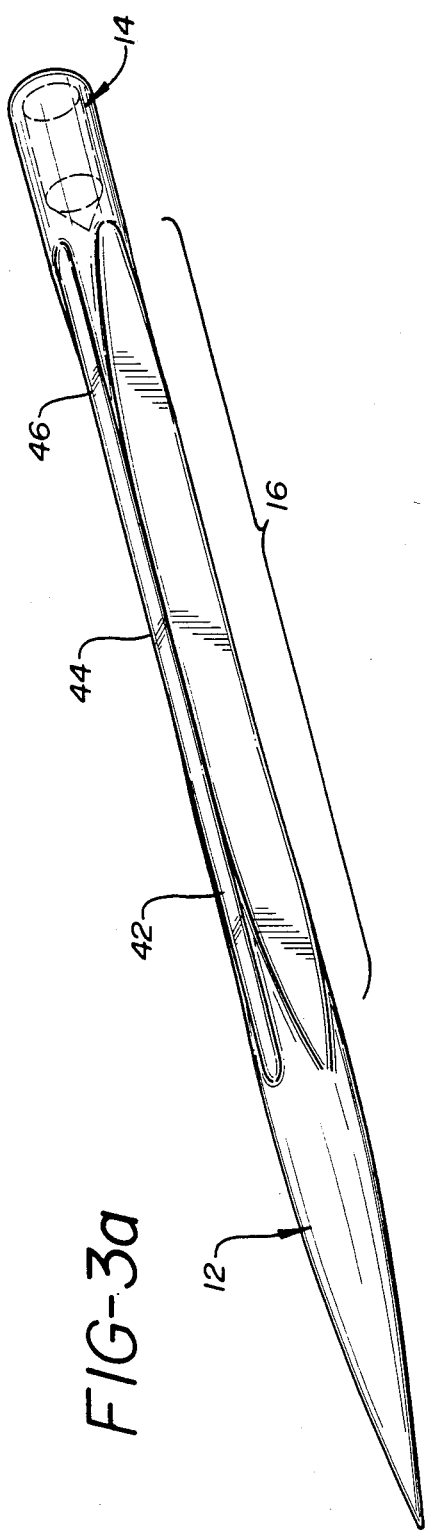
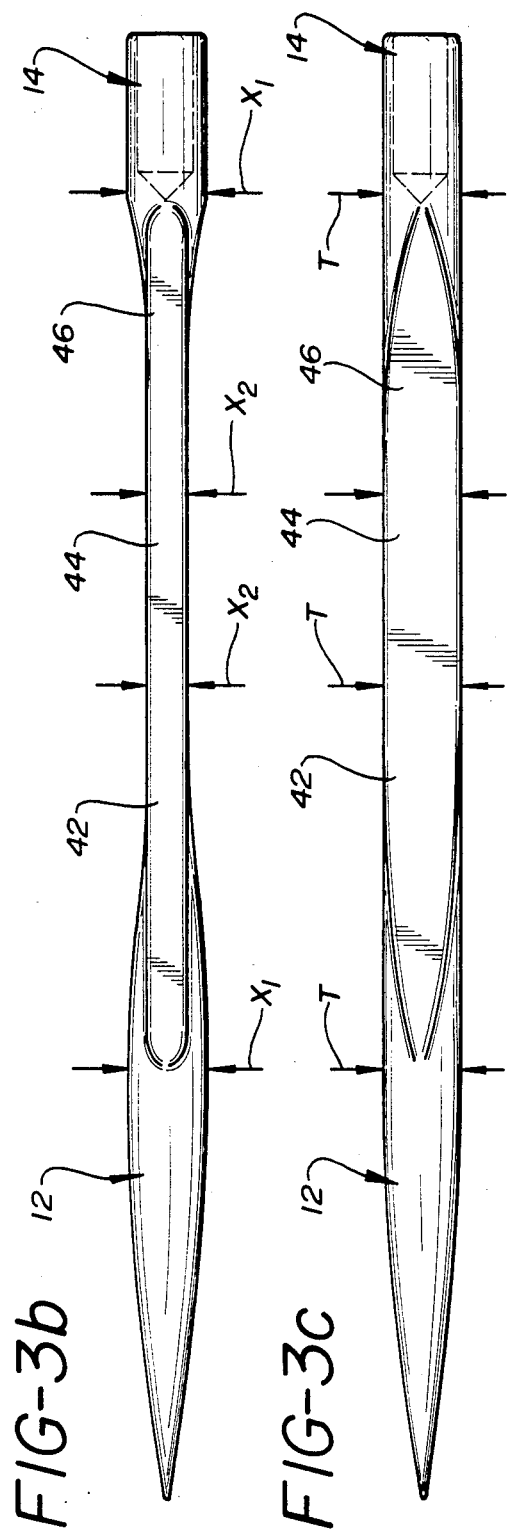

TAPERED I-BEAM SURGICAL NEEDLES

This invention relates to surgical needles and, in particular, to such needles having a generally rectangular cross-sectional area such needles being referred to herein as "I-beam" needles.

In the design of surgical needles it is generally desirable for needles to exhibit favorable characteristics in two areas: strength and ease of penetration. It is desirable for a surgical needle to be strong enough to penetrate tissue which is being sutured without bending or breaking during a surgical procedure. It is also desirable for the needle to easily penetrate and smoothly pass through the tissue being sutured. The ease of penetration is dependent upon more than just the sharpness of the needle. Once the needle point has penetrated the tissue, the body of the needle must be drawn through the opening in the tissue. This should be done with minimal force, and the needle should be shaped so that it will move smoothly through the opening, without binding occurring along the body of the needle. The needle should be designed so as to minimize the resistance of the tissue to the passage of the entire needle through the tissue. Furthermore, the passage of the needle through the tissue should cause no more than minimal traumatization to the tissue. When the passage of the needle through the tissue is accomplished smoothly through a small opening in the tissue, the surrounding tissue is left relatively undamaged, which promotes ease of healing of the sutured tissue.

The design techniques generally employed to meet these two design criteria of strength and ease of penetration are often in conflict, however. One straightforward approach to improve the strength of a needle, for instance, is to increase its diameter, or thickness. But by increasing the thickness of the needle, the force necessary to penetrate the tissue is also increased, and the opening left in the tissue after passage of the needle is also enlarged. Likewise, penetration ease can be improved by making the needle thinner, but this approach will correspondingly reduce the needle's strength. Thus the design of a needle with favorable performance in both areas often requires that tradeoffs be made in the two criteria to arrive at a needle with optimal overall performance.

In accordance with the principles of the present invention, a surgical needle is providing having a point section, a barrel section for attachment to a suture, and an intermediate body section, at least a portion of which exhibits an I-beam cross-section. As is well known, I-beam cross-sectional needles provide favorable strength characteristics by reason of their relatively large "T" dimension, which is the larger height of the rectangular cross-section. To provide the strength of an I-beam needle, but with improved penetration characteristic, the needles of the present invention exhibit a gradual taper from a non-I-beam shape to an I-beam shape. This taper is characterized by a changing width along the length of the taper in one lateral dimension of the I-beam, and an unchanging width in the other lateral dimension. Such a taper is characterized by a smooth transition from rounded corners at the beginning of the taper to sharply defined corners as the I-beam shape is achieved. The transition in corner shape provides a feature whereby only minimal increases in penetration force are required as the body of the needle is drawn through the tissue opening made by the point of the needle. The needle thus affords the strength of an I-beam needle without the usual corresponding adverse effect on needle performance In the drawings:

FIGS. 1a–1c illustrate a surgical needle of the present invention with a continuously tapered body section;

FIGS. 2a–2c illustrate a surgical needle of the present invention in which the body section comprises a tapered portion and an I-beam portion of constant dimension;

FIGS. 3a–3c illustrate a surgical needle of the present invention in which the body section comprises two tapered portions separated by an I-beam portion of constant dimensions;

FIGS. 5a–5h illustrate various cross-sectional areas of surgical needles.

Needles for surgical uses may exhibit any of a variety of well-known shapes. For example, there is the well-known circular cross-sectional shape shown in FIG. 5a. Such needles are desirable for the relatively low force required to pass the smooth, circular shaped needles through tissue. Various other curved shapes, such as oval or elliptical shapes, have also been used for surgical needles.

Figure 5A:
Figure 5B:
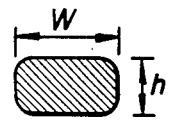
Figure 5C:
Figure 5B:
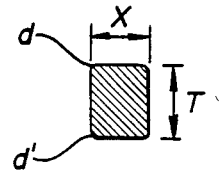

Another well-known shape for the body of a surgical needle is the so-called "ribbon" shape shown in FIG. 5b. The ribbon shape is formed by compressing a round needle on two opposite sides. Ribbon body needles are relatively weak, due to the lesser h dimension as compared with the w dimension. A square body needle, represented in cross-section in FIG. 5c, provides an improvement in strength by reason of its geometry as compared with the ribbon body. When the square body needle is viewed in cross-section, its significant height relative to the center line of the needle provides a favorable moment of inertia, or bending moment.

An even greater improvement in strength is provided by the rectangular or I-beam needle, represented in cross-section in FIG. 5d. The basis of the strength of the I-beam needle is due to the relatively larger "T", or height dimension from corner d to corner d'. However, the penetration performance of the I-beam needle is relatively poor, due to the force required for the square corners of the needle to penetrate tissue. An approach that has been taken to improve the I-beam needle's penetration performance is to round the corners of the I-beam, as shown in the cross-sectional representation of FIG. 5e (scale enlarged). However, the rounding of the corners also reduces the moment of inertia above the center line, thereby adversely affecting the strength of the I-beam needle.

An embodiment of a surgical needle made in accordance with the principles of the present invention is shown in FIGS. 1a–1c. This embodiment addresses the design trade-offs affecting strength and performance with its unique tapered body section. The needle 10 of FIG. 1a has three component sections, a point section 12, a barrel section 14, and an intermediate body section 16. The needle is made of any of the conventionally available materials for surgical needles, including stainless steel and carbon steel, with stainless steel being a preferred material. The production of the needle begins with a straight piece of wire of the needle material, which may be hardened or treated by any of the well-known processing techniques for performing these operations. The point section 12 is formed by grinding, pressing or other commonly known techniques. The barrel section contains a hole 18 in which a suture is to be fastened by swaging or adhesive attachment. Alternatively, the barrel section may contain a V-shaped channel into which the suture is placed for swaging.

The body section 16 of needle 10 exhibits a shape which gradually varies from a round cross-sectional shape at the point section to a sharply cornered I-beam shape at the barrel section. This transition in shape gives the needle four orthogonally oriented flat sides: a top 26, a bottom 28, and opposite sides 22 and 24. The dimension between the top 26 and bottom 28 is shown in the drawing as height dimension T, and the width between sides 22 and 24 is shown as width x. As the shape of the needle body varies from round at the point end to I-beam at the barrel end, the height T remains constant. The width x, however, gradually decreases over the length of the body section as the barrel section is approached. The effect of these differences in shape are shown in the plan views of FIGS. 1b and 1c. FIG. 1b is a view facing the bottom 28, which shows the variation in width x along the length of the needle. FIG. 1c is a view facing the side 24 of the needle, which shows the constant height T of the needle.

In the design of I-beam surgical needles, conventional wisdom would be to begin the I-beam shape as promptly as possible after termination of the point section, and to continue the I-beam shape as far as possible along the length of the body section until a transition must be made to the shape of the barrel section. This conventional technique dictates that short transitions in shape be made where the I-beam shape begins and ends. These short transitional regions are commonly referred to as "blends" or "runouts." Two such runouts are shown at either end of the I-beam portion in the center of the needle of U.S. Pat. No. 3,197,997. In contrast to these abrupt runouts, surgical needles of the present invention provide a continuously smooth transition in shape over the entire tapered portion of the body section. The benefits provided thereby are twofold. First, as explained above different needle shapes provide different strength characteristics. The needle of FIGS. 1a–1c will exhibit one strength characteristic at the back of the point section where the cross-section of the needle is rounded, and a different strength characteristic at the back of the body section where the needle exhibits its distinctly I-beam shape. The continuously varying taper between these two regions will provide a smooth variation in strength characteristics between these two regions of different shape. This eliminates any sharp transition in shape with its corresponding sharp change in strength characteristics, which can give the needle a propensity to bend at such a point of the needle.

Figure 5E:
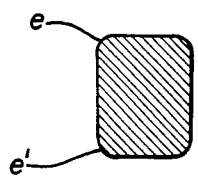
Figure 5F:

Secondly, the smoothly varying transition in shape provides a smooth transition in performance characteristics, as opposed to the sudden change in performance characteristics which accompanies a short blend or runout. Referring to FIGS. 5a–5g, cross-sectional views taken along the length of the surgical needle of FIG. 1a are shown. FIG. 5a shows the circular shape of the needle at the back of the point section 12, just before the tapered body. FIG. 5f illustrates the shape of the needle at the start of the tapered body, just as the flattened sides commence. As this FIGURE shows, the needle at this point is just starting to assume an I-beam shape. The needle is still substantially round, with very rounded corners between the small orthogonal flat sides. The greatly rounded corners provide an ease of penetration which is almost as favorable as the fully rounded needle shape at the back of the point section. The greatly rounded corners exhibit substantially the same curvature as the rounded circumference at the termination of the point section.

Figure 5G:
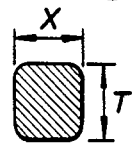

Continuing along the length of the body section toward the barrel section, FIG. 5g illustrates the shape of the body section as the I-beam shape is approached. At this point, the strength of the needle is increasing as the needle shape approaches the desired I-beam shape. The corners of the needle are still rounded with substantially the curvature of the needle at the point section. These rounded corners continue to afford a commensurate ease in needle penetration.

At the back of the body section, the full I-beam shape is achieved, as illustrated in FIG. 5d. At this point the I-beam shape with its square corners affords the full strength characteristic of this cross-sectional shape.

It may thus be seen that the tapered shape provides a smooth transition in needle characteristics along the needle taper. In needles of the prior art, with their relatively short blends and runouts between areas of different shape, the transition in needle characteristics is correspondingly abrupt. In the case of needle penetration performance a surgeon who is pushing a prior art needle through tissue will feel slight "surges" and "grabbing" as the short transitional regions encounter the tissue. The surges and grabbing distract from the suturing operation and can result in uneasy and uneven wound closure by reason of uneven needle performance. The surgical needles of the present invention overcome these operational difficulties by providing a strong needle with a smooth distribution of changes in penetration force over the length of the taper. This enhances the perception of the surgeon that the needle is smoothly penetrating and passing through tissue.

When the length of the needle so permits it may be desirable to employ both a tapered portion and an I-beam portion along the needle body. Referring to FIG. 2a–2c, a surgical needle is shown having a point section 12, a barrel section 14 and an intermediate body section 16. At the jointure of the point and body sections, the needle begins to taper and make a gradual transition from a round shape to an I-beam shape. Along this tapered portion 30, the x dimension of the needle varies from $X_1$ to a smaller dimension $X_2$, while the T dimension remains constant. When the I-beam shape is achieved at point $X_2$, the body section maintains the I-beam shape along portion 32 of the body section. At the back of the body section, a runout changes the shape of the needle from I-beam to the rounded shape of the barrel section. The surgical needle of FIGS. 2a–2c thus exhibits a tapered body portion 30 of smoothly varying strength and performance characteristics, and an I-beam body portion 32 of characteristically high strength.

It may be seen that the surgical needles of FIGS. 1a and 2a have a runout at the jointure of the body section 16 and the barrel section 14, where the shape of the needle makes the transition from I-beam to round. However, the round barrel section will generally pass smoothly through the hole made by the point section, as the size and shape of the barrel section 14 is generally the same as that at the back of the point section. An embodiment of the present invention which eliminates even this short transition in shape is shown in FIGS. 3a–3c. The needle there shown has a point section 12, a barrel section 14 and an intermediate body section 16.

The body section exhibits three distinctly shaped regions, a forward tapered region 42, an intermediate I-beam region 44, and a rearward tapered region 46. As shown in the views of FIGS. 3b and 3c, the forward tapered region 42 starts from the jointure of the point and body sections where the needle has a circular shape and $X_1 = T$. As the taper extends toward the middle of the needle, the T dimension remains constant and the x dimension decreases from $X_1$ to $X_2$ until the I-beam shape is achieved at the first point marked $X_2$. The central region 44 of the body exhibits an I-beam shape of constant dimensional characteristics. At the back of the I-beam region 44 the needle begins a reverse taper and change in shape from I-beam to circular diameter. Along the rearward tapered region 46 the X dimension increases from $X_2$ to $X_1$, and the T dimension remains constant. At the back of the rearward tapered region where the body section ends, $X_1$ is equal to T and the needle again exhibits its round shape, which continues along the barrel section 14. The surgical needle of FIGS. 3a-3c thus exhibits smoothly varying strength and performance characteristics along its entire length with no sudden changes due to runouts or blends. At the jointures of the body section and the point and barrel sections, the needle exhibits round corners having a curvature which approaches the radius of the completely circular portions of the needle. At the vicinity of the I-beam region 44, the surgical needle exhibits sharp corners having a radius ranging from 0.002 inches for smaller gauge wire to 0.008 inches for larger gauge wire. In order to more fully realize the strength and performance characteristics of the present invention it is preferable for at least 50% of the total length of the body section of the needle to exhibit the characteristic taper.

Figure 4:
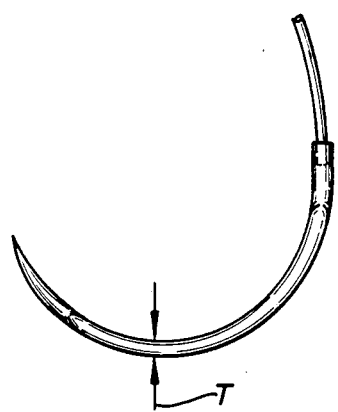
FIG. 4 illustrates a curved surgical needle constructed in accordance with the principles of the present invention.

FIG. 4 illustrates a curved needle 50 constructed in accordance with the principles of the present invention. The curved needle 50 is made by first producing the needle of FIG. 1a, wherein a piece of wire is pointed, drilled and flattened on its orthogonal sides to produce the tapered needle of that FIGURE. The straight tapered needle is then curved using a conventional radius tool. The curving is performed with the needle oriented so that its greater T dimension is in the plane of the finished curved needle. This larger dimension of the tapered I-beam needle will thus resist forces which would tend to bend the needle from its curved shape during use. The curved needle of FIG. 4 is continuously tapered over its full length from the termination of the point section to the beginning of the swage, or barrel section.

Figure 5H:

To demonstrate the strength and performance advantages of the surgical needles of the present invention several different needles were fabricated and tested. A baseline reference for these characteristics was established by testing a square needle having a point section, with the remainder of the needle exhibiting a cross-sectional shape as shown in FIG. 5h. This reference needle was made in the conventional manner by compressing a pointed round needle on its four sides, leaving four flattened sides with slightly rounded corners. The shape of FIG. 5h was blended into the round shape at the jointure of the body and point sections of the needle. The reference square needle was compared with two I-beam needles and a tapered I-beam needle of the present invention. One of the I-beam needles had sharp corners as shown in cross-section in FIG. 5d. This shape was blended into the round shape of the point section and extended to the end of the barrel section. The other I-beam needle had rounded corners as illustrated in FIG. 5e. This shape also was blended into the point section and extended to the barrel end of the needle. The tapered I-beam needle was tapered to a sharp-cornered I-beam shape at the beginning of the barrel section.

These needle samples, which were siliconized over approximately one-half of the needle length, were tested for ease of penetration on an Instron Model 1125 machine, which measured the forces required to penetrate a 10 mil sheet of polyurethane, designated type MP 1880 and available from J. P. Stevens & Co. of Northampton, Mass. A comparison of the maximum forces recorded to pass the unique needle geometries through the test material showed that the I-beam needle with rounded corners required 10% more penetration force than the tapered I-beam needle. The I-beam needle with sharp corners required 18% more penetration force than the tapered I-beam needle. The square reference needle with rounded corners required an equivalent amount of penetration force as the tapered I-beam needle, as the test results of these two samples were within 1.6%.

The needle samples were then bend tested for strength in a bend testing machine. Each needle was clamped in a rotatable test fixture with the point contacting a fixed load cell, the output of which was connected to a recording instrument. A constant dimension was maintained between the needle point and the point of attachment in the test fixture. In the case of a curved needle, a constant chord length is maintained from needle to needle. The test fixture holding the needle was then rotated through an angle of 90° about the load cell, and the bend force was recorded. The bend strength was then measured at the yield point for each needle. The results of this testing showed that, as expected, the I-beam needles were stronger than the square reference needle. The I-beam needle with rounded corners was 13% stronger than the reference needle, and the I-beam needle with sharp corners was 19% stronger. The tapered I-beam needle was 17% stronger than the reference needle, which is better than the rounded corner I-beam needle but not quite as strong as the sharp-cornered I-beam needle.

It is thus seen that the tapered I-beam needle design of the present invention affords an efficient compromise of the desired characteristics of high strength and ease of penetration.

What is claimed is:

1. A tapered surgical needle comprising a point section, a barrel section, and an intermediate body section joining the point and barrel sections, said point section exhibiting a rounded circumference at its terminus at the body section, said body section exhibiting, over a substantial portion of its length, a tapered region over which the shape of the needle undergoes a gradual transition from a rounded circumference at one end of said tapered region, to a rectangular cross-sectional shape at the other end of said tapered region, and a subregion intermediate said tapered region over which said tapered region exhibits a transition from a generally rectangular cross-sectional shape with four flat sides and rounded corners to a rectangular cross-sectional shape with sharp corners.

2. The tapered surgical needle of claim 1, wherein said rectangular shape is characterized by a needle width dimension x and a greater needle height dimension T, said rounded circumference exhibits a needle diameter D, and T is substantially equal D and x is less than D.

3. The tapered surgical needle of claim 2, wherein, over the transition of said tapered region, the needle maintains a substantially constant dimension in the direction of the height T of the rectangular shape, and the needle decreases in dimension in the direction of the width x as the transition is made from said rounded circumference to said rectangular shape.

4. The tapered surgical needle of claim 3, wherein said tapered region is substantially equal to the length of said body section, and wherein said needle makes a short transition in shape from said rectangular shape to the shape of said barrel section in the form of a blend or runout.

5. The tapered surgical needle of claim 2, wherein said body section further exhibits, over a length of said needle extending from the generally rectangular shape of said tapered region, a region of substantially constant rectangular shape.

6. The tapered surgical needle of claim 5, wherein said region of substantially constant rectangular shape exhibits a needle width x and a greater needle height T.

7. The tapered surgical needle of claim 6, wherein said region of said body section of substantially constant rectangular shape terminates at said barrel section, at which location said needle makes a short transition in shape from said substantially constant rectangular shape to the shape of said barrel section in the form of a blend or runout.

8. The tapered surgical needle of claim 1, wherein said point section, said barrel section, and said intermediate body section are coaxially curved in a continuous arcuate shape.

9. The tapered surgical needle of claim 1, wherein said point and barrel sections exhibit generally rounded circumferences, said tapered region extends from the terminus of said point section toward said barrel section, and further comprising a second tapered region over which the shape of the needle undergoes a gradual transition from the generally rounded circumference of said barrel section to a generally rectangular shape at the other end of said second tapered region remote from said barrel section.

10. The tapered surgical needle of claim 9, wherein, over the transition of said second tapered region, the needle maintains a substantially constant dimension T equal to the diameter of said barrel section and the height of said generally rectangular shape of said second tapered region, and the needle decreases in an orthogonal direction of x from the diameter of the barrel section to the width x of said generally rectangular shape of said second tapered region.

11. The tapered surgical needle of claim 10, further comprising intermediate said first-named and second tapered regions, a region of substantially constant rectangular shape.

12. The tapered surgical needle of claim 11, wherein the heights of the generally rectangular shape of said first-named and second tapered region and the height of said region of substantially constant rectangular shape are all equal; and the width of the generally rectangular shape of said first-named and second tapered region and the width of said region of substantially constant rectangular shape are all equal.

* * * * *